(12) United States Patent
Quinn (10) Patent No.: US 7,914,497 B2
(45) Date of Patent: Mar. 29, 2011

(54) CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 844 days.

(21) Appl. No.: 11/339,660

(22) Filed: Jan. 25, 2006

(65) Prior Publication Data

US 2006/0167406 A1    Jul. 27, 2006

Related U.S. Application Data

(60) Provisional application No. 60/647,254, filed on Jan. 26, 2005.

(51) Int. Cl.
*A61M 29/00*    (2006.01)

(52) U.S. Cl. .......................... 604/174; 604/175; 604/910

(58) Field of Classification Search .................. 604/910, 604/918, 919, 174, 175; 128/DIG. 26
See application file for complete search history.

(56) References Cited

U.S. PATENT DOCUMENTS

| | | | |
|---|---|---|---|
| 4,356,824 A | 11/1982 | Vazquez |
| 4,533,349 A | 8/1985 | Bark |
| 4,543,089 A | 9/1985 | Moss |
| 4,642,092 A | 2/1987 | Moss |
| 4,666,433 A | 5/1987 | Parks |
| 4,668,225 A | 5/1987 | Russo et al. |
| 4,685,901 A | 8/1987 | Parks |
| 4,699,616 A | 10/1987 | Nowak et al. |
| 4,701,163 A | 10/1987 | Parks |
| 4,717,385 A | 1/1988 | Cameron et al. |
| 4,795,430 A | 1/1989 | Quinn et al. |
| 4,900,306 A | 2/1990 | Quinn et al. |
| 4,981,471 A | 1/1991 | Quinn et al. |
| 5,073,166 A | 12/1991 | Parks et al. |
| 5,125,897 A | 6/1992 | Quinn et al. |
| 5,248,302 A | 9/1993 | Patrick et al. |
| 5,267,967 A | 12/1993 | Schneider |
| 5,267,968 A | 12/1993 | Russo |
| 5,308,325 A | 5/1994 | Quinn et al. |
| 5,318,530 A | 6/1994 | Nelson, Jr. |
| 5,324,260 A | 6/1994 | O'Neill et al. |
| 5,342,321 A | 8/1994 | Potter |
| 5,374,254 A | 12/1994 | Buma |
| 5,439,444 A | 8/1995 | Andersen et al. |
| 5,451,212 A | 9/1995 | Andersen |
| 5,484,420 A | 1/1996 | Russo |
| 5,556,385 A | 9/1996 | Andersen |
| 5,662,622 A | 9/1997 | Gore et al. |
| 5,690,616 A | 11/1997 | Mogg |

(Continued)

OTHER PUBLICATIONS

Ross Products Division, Abbott Laboratories, Flexiflo®, Inverta-PEG™, 1994.

(Continued)

*Primary Examiner* — Nicholas D Lucchesi
*Assistant Examiner* — Laura A Bouchelle
(74) *Attorney, Agent, or Firm* — Brinks Hofer Gilson & Lione (57) ABSTRACT

A catheter includes a catheter tube, internal and external retention bolsters and a retractable catheter tip. The retractable tip is in the form of a bolus which is extended to axial alignment with the tube for insertion. After insertion with a stylet or the like, removal of the stylet permits the tip to retract automatically and assume a position perpendicular to the axis with minimal protrusion into the corporeal space involved.

12 Claims, 7 Drawing Sheets

U.S. PATENT DOCUMENTS

| | | |
|---|---|---|
| 5,709,691 A | 1/1998 | Morejon |
| 5,718,691 A | 2/1998 | Russo |
| 5,720,734 A | 2/1998 | Copenhaver et al. |
| 5,810,787 A | 9/1998 | Quinn |
| 5,860,952 A | 1/1999 | Quinn |
| 5,865,816 A | 2/1999 | Quinn |
| 5,891,113 A | 4/1999 | Quinn |
| 5,910,128 A * | 6/1999 | Quinn .................. 604/93.01 |
| 6,066,112 A | 5/2000 | Quinn |
| 6,077,243 A | 6/2000 | Quinn |
| 6,364,858 B1 * | 4/2002 | Picha ..................... 604/174 |

OTHER PUBLICATIONS

Corpak, Inc., Inflation/Deflation Mechanics, 1991.

Faller, Nancy et al., "Comparing Low-Profile Gastrostomy", *Nursing*, Dec. 1993.

* cited by examiner

Fig. 26    Fig. 27 form desired functions without becoming occluded or dam-
CATHETER

RELATED APPLICATION

This application is based on provisional application Ser. No. 60/647,254, filed Jan. 26, 2005, and claims priority therefrom. The provisional application is incorporated herein by reference in its entirety.

FIELD OF THE INVENTION

This invention relates generally to catheters for introducing fluids to body cavities and/or exhausting fluids from body cavities. It relates particularly to what are commonly referred to as balloon catheters, which find particularly advantageous application in aspirating or draining fluid from the stomach or bladder. The invention applies to catheters employing preformed, thick-walled balloons or thin walled balloons requiring stretching to their final shape by the instillation of liquid or air.

BACKGROUND OF THE INVENTION

Whether employed in bladder draining, as with the Foley catheter, or enteral feeding applications, catheters must perform desired functions without becoming occluded or damaging the organ walls, if that is possible. Unfortunately, it is frequently not possible for extended periods of time with conventional catheters. Foley urologic tips and enteral percuteneous replacement catheters all employ tips with side ports. The tips extend as a length of tubing from the base of the catheter retention balloon. The tips poke into the mucosa of the bladder or stomach causing pressure necrosis. In some instances they actually penetrate the organ wall which results in leakage of fluid and subsequent infection. Conventional tips are also subject to restriction of flow in the aspiration mode because the side ports are sucked into the vessel wall mucosa, thereby occluding flow. This "sucking" phenomenon also results in suction sores at the point of contact, resulting in focal points for infection.

SUMMARY OF THE INVENTION

An object of the invention is to provide a new and improved catheter.

Another object is to provide a new and improved catheter including a catheter tube, a retention bolster and a retracting bolus tip.

Another object is to provide a catheter including an automatically retracting bolus tip that, in use, does not protrude into a corporeal space to the extent that it can cause necrosis and subsequent erosion of the cavity wall.

Still another object is to provide a catheter of the aforedescribed character with a bolus tip which facilitates simple insertion with a stylet and, upon withdrawal of the stylet, the bolus automatically retracts.

Yet another object is to provide a catheter which, during insertion with a stylet, presents a rounded tip that facilitates insertion and prevents abrasion.

A further object is to provide a catheter including a retracting bolus tip that allows aspiration or drainage without suction retention.

Yet a further object is to provide a catheter of the aforedescribed character including a bolus tip that effectively prevents occlusion of the catheter port by mucosa.

Yet another object of the invention is to provide an external bolster that provides the maximum in a low profile shape.

Yet another object of the invention is to provide an external bolster that provides a soft retention surface that spreads retention pressure over its entire surface and reduces soreness and infection at the site of the external stoma.

Yet another object of the invention is to provide an external bolster that provides the ability to lift the bolster for cleansing.

Yet another object of the invention is to provide an external bolster that provides for a method of presenting a slit valve contained in the external bolster that allows for the inflation/deflation of the internal retention bolster while at the same time not increasing the size of the external bolster.

Yet another object of the invention is to provide an external bolster that acts as a "monitor" for the inflation of the internal bolster.

Yet another object of the invention is to provide an external bolster that provides for an easy method of deflating the internal bolster.

The invention also incorporates an external inflatable retention device that secures the catheter while at the same time presenting soft, but strong retention because it is inflated with air and its round shape spreads the retention pressure over a large area. External bolsters should be "low profile" so that they do not interfere with the patient's clothing and are inconspicuous. The new external bolster offers a lower profile than any of the existing devices.

The device incorporates a unique insertion tip with a preformed inflatable bolster and also a unique external inflatable retention bolster. Both bolsters are in communication with each other and therefore have the same internal air pressures.

BRIEF DESCRIPTION OF THE DRAWINGS

The invention, including its construction and method of operation, is illustrated more or less diagrammatically in the following drawings, in which.

DESCRIPTION OF THE PREFERRED EMBODIMENT

Referring now to the drawings and particularly to FIGS. 1-6 the distal end of a catheter embodying features of the invention is seen generally at 10. The catheter illustrated includes a 20 French (20 Fr) catheter tube 12 molded of a soft, resilient plastic such as silicone. Secured to the corresponding end of the tube 12 is a retention balloon bolster 14 and a bolus tip 16, molded unitarily from the same plastic.

Figures 5, 6, 7:
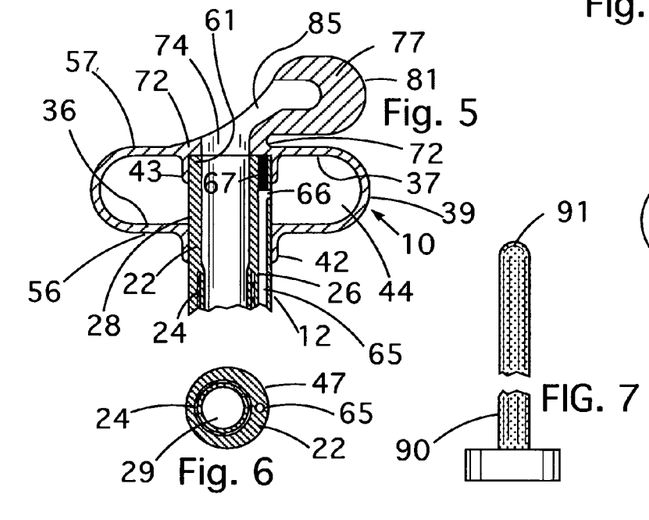
FIG. 5 is a sectional view taken along line 5-5 of FIG. 3.
FIG. 6 is a sectional view taken along lines 6-6 of FIG. 1.
FIG. 7 is a front elevational view of a stylet used in conjunction with the catheter of the invention to introduce the catheter into a body cavity.

Referring specially to FIGS. 5 and 6, the tube 12 comprises a silicone body 22 containing a stainless steel wire coil spring 24. The coil spring 24 extends from a suitable set connector on the proximal end of the tube 12 (not shown) to a location 26 immediately adjacent the retention balloon bolster 14. Accordingly, the balloon bolster 14 surrounds the tube portion 28 which is not supported by the spring 24. The tube body 22 is formed with the spring 24 in it in the manner described in Quinn U.S. Pat. No. 6,077,243. A lumen 29 extends through the length of the tube body 22.

The retention bolster 14 comprises a tire-shaped balloon 20. The tire-shaped balloon 20 is preformed in that shape from silicone rubber and includes parallel sidewalls 36 and 37. The sidewall 37 is the rear sidewall while the sidewall 36 is the front sidewall. Connecting the sidewalls 36 and 37 (in the language of tire construction) is the treadwall 39. The treadwall 39 is semi-circular in cross-section.

The annular inner peripheries of the sidewalls 36 and 37 are defined by beads 42 and 43, respectively. Each of the beads 42 and 43 comprises a cylindrical sleeve. The sleeve 43 extends forwardly of the rear sidewall 37. Thus, it is inside the balloon 20. The sleeve 42 extends forwardly of the front sidewall 36. Thus, it is outside the balloon 20. The cylindrical inner surfaces of the sleeves 42 and 43 are glued to the outer surface of the tube body 22 wall with a silicone adhesive.

Air is trapped in the space 44 within the preformed balloon 20 when the bead sleeves 42 and 43 are glued to the body 22 to assemble the tube 12 and balloon 20. The front and rear sidewalls 36 and 37 extend parallel to each other from their corresponding bead sleeves 42 and 43 to their juncture with the semi-circular treadwall 39. A flat front surface 56 is, accordingly, defined on the outside of the front wall 36 while a flat rear surface 57 is defined on the outside of the rear wall 37.

According to the invention, the flat front surface 56 forms the balloon 20 retention surface for the catheter 10. The flat rear surface 57 is flush with the tube 12 at its port 61. Thus, the tube 12 does not protrude forwardly beyond the balloon 20.

The body 22 of the tube contains a deflation lumen 65 which extends the length of the tube segment between the coil spring 24 and the outer surface 47 of the tube body. The deflation lumen 65 communicates with the inside of the balloon 20 through a radial aperture 66 in the tube segment body 41. The lumen 65 is plugged at 67 under the balloon bead 63. It is also plugged adjacent its opposite end, i.e., normally at the aforementioned set connector (not shown).

As has been pointed out, the bolus tip 16 is molded unitarily with the retention balloon bolster 14. The tip 16 comprises a cylindrical base 72 defining a port 74, the port being co-axial with, and having the same ID (inside diameter) as that of the tube lumen 29.

Cantilevered to one side of the cylindrical base 72 is the bolus tip nose section 77. The nose section 77 includes a bullet nose 79 having a semi-spherical outer surface 81 and an internal socket 83.

Bracketing the socket 83, and extending radially inwardly toward the axis of the cylindrical base 72, are opposed side walls 85 and 86. The side walls 85 and 86 have corresponding upper edges 88 and 89 which slope gradually toward the cylindrical base 72 and join it on opposite sides of the lumen port 61.

Figure 8:
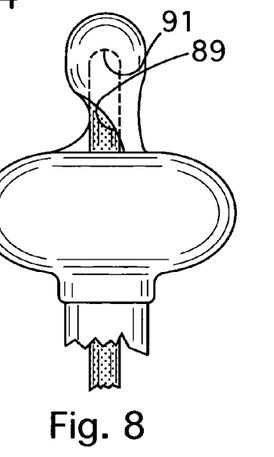
FIG. 8 is a front elevational view, similar to FIG. 1, showing the stylet in the catheter and holding the bolus in its extended position for insertion.

To place the catheter 10 in a patient's bladder through the urethra or into the stomach through a stoma, the nose section 77 of the bolus tip 16 is manually moved to the position shown in FIG. 8, i.e., into its extended position. A stylet 90, such as seen in FIG. 7, is then inserted through the tube 12 from its proximal end (not shown) until the end 91 of the stylet is seated in the socket 83 of the bolus tip nose section 77.

A plug (not shown) in the air passage 65 near the proximal end of the tube 12 is removed so that air can escape from the balloon 20. Accordingly, when the stylet 90 is employed to insert and push the catheter through a stoma, for example, the tube portion 28 stretches, the balloon 20 elongates axially and shrinks radially to where the bolster 14 and bolus tip pass through the stoma.

With the catheter 10 in place, the stylet 90 is pulled out. The balloon 20 resumes its normal shape. The tip 16 retracts to the position shown in FIGS. 1-5. A plug is reinserted in the lumen 65 near the set connector. The catheter 10 is operational.

Figure 1:
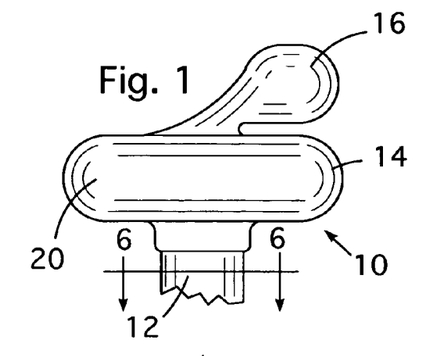
FIG. 1 is a side elevational view of the distal end of a catheter embodying features of the present invention, showing its bolus tip in a normal retracted position.
Figure 2:
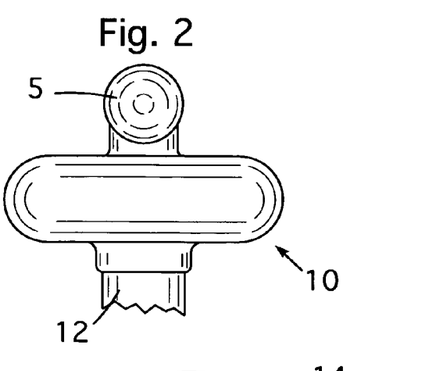
FIG. 2 is a rear elevational view of the catheter end seen in FIG. 1.
Figure 3:
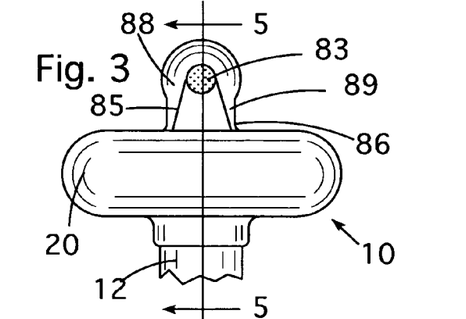
FIG. 3 is a front elevational view of the catheter end seen in FIG. 1.
Figure 4:
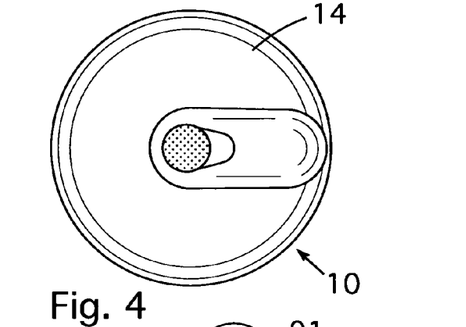
FIG. 4 is a top plan view of the catheter end seen in FIG. 1.
Figures 9, 10, 11, 12, 13, 14:
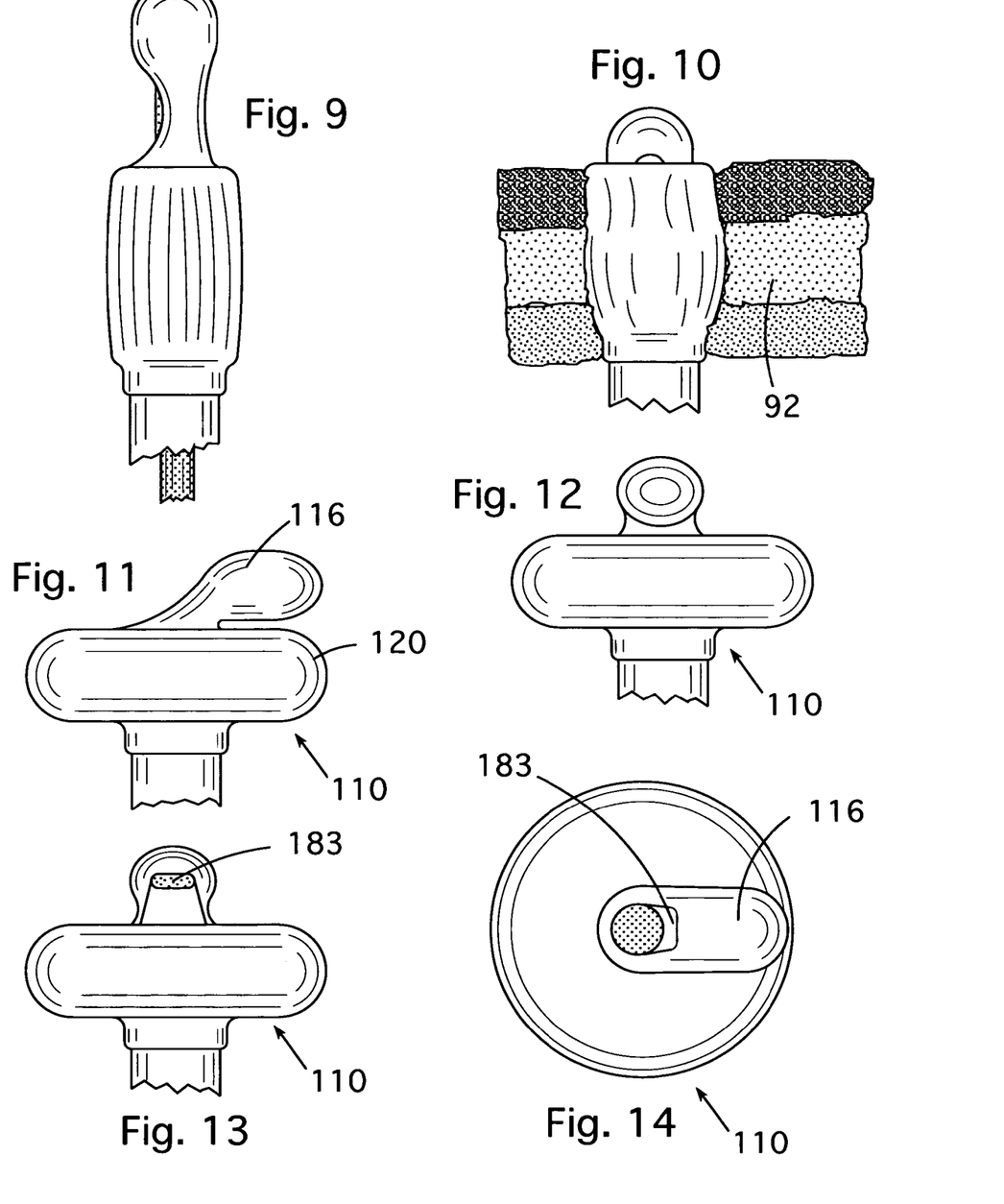
FIG. 9 is a front elevational view of the catheter, similar to FIGS. 1 and 8 showing the retention balloon fully stretched by the stylet for insertion.
FIG. 10 is a front elevational view of the catheter, similar to FIG. 1 showing the retention balloon folded back on itself during removal.
FIG. 11 is a side elevational view of the distal end of another catheter as shown in FIG. 1, but with a lower elevation from the retention balloon and a smaller mass.
FIG. 12 is a rear elevational view of the catheter end as seen in FIG. 11.
FIG. 13 is a front elevational view of the catheter end as seen in FIG. 11.
FIG. 14 is a top plan view of the catheter as seen in FIG. 11.

Referring now to FIGS. 11-14, another embodiment of the catheter end shown in FIG. 1 is shown at 110. The function and operation of the two versions 110 and 10 are identical. FIG. 13 shows the socket 183 that has an oblong shape rather than the round shape of socket 83. In the case of socket 83 the stylet 90 is the approximately the same size and shape as the socket 83. The socket 183 has an oblong shape that has the same internal cross sectional area as socket 83. When stylet 90 is inserted into socket 183 the bullet bolus tip 116 expands to accept the stylet 90. Socket 83 is a circle with an outside diameter of 0.066." Socket 183 has a height of 0.030" and a width of 0.093.

Figure 15:
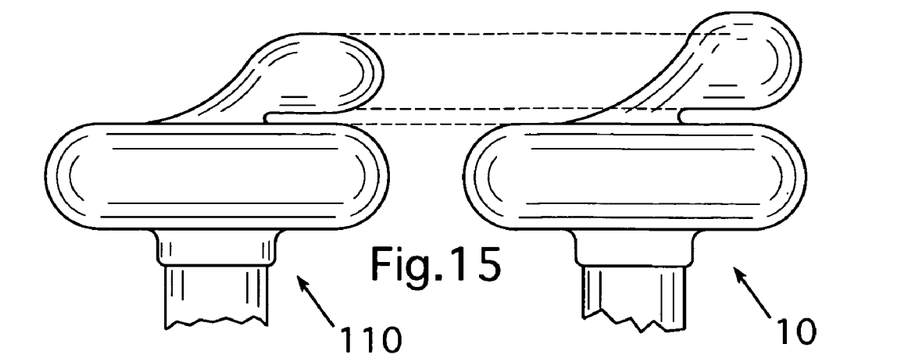
FIG. 15 is a side elevational view of the distal catheter ends as shown in FIG. 11 showing the relative masses.
Figure 16:
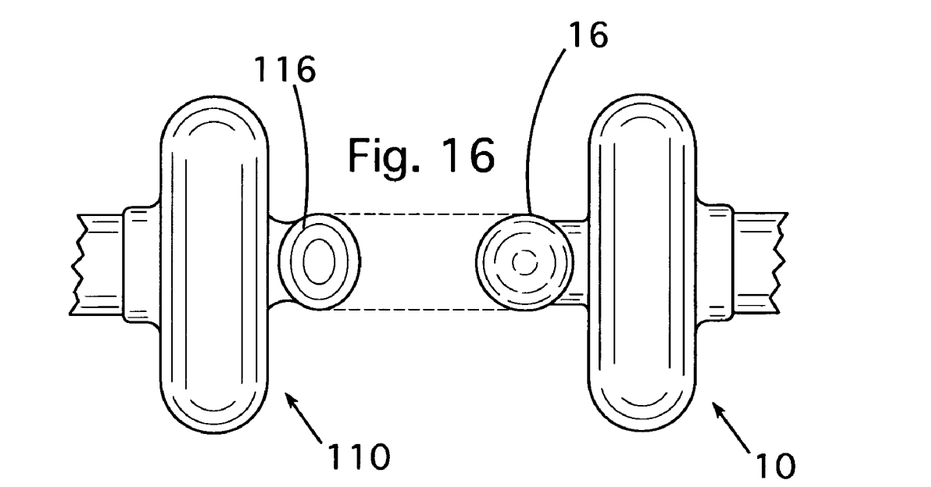
FIG. 16 is a rear elevational view of the distal catheter ends as shown in FIGS. 2 and 12 showing the widths of the bullet tips.

The catheter end 110 provides a lower profile when in place in the body cavity. FIG. 15 shows the lower comparable height of bullet tip bolus 16 in place. FIG. 16 shows that the width of bullet tip boluses 16 and 116 are the same width.

Figure 17:
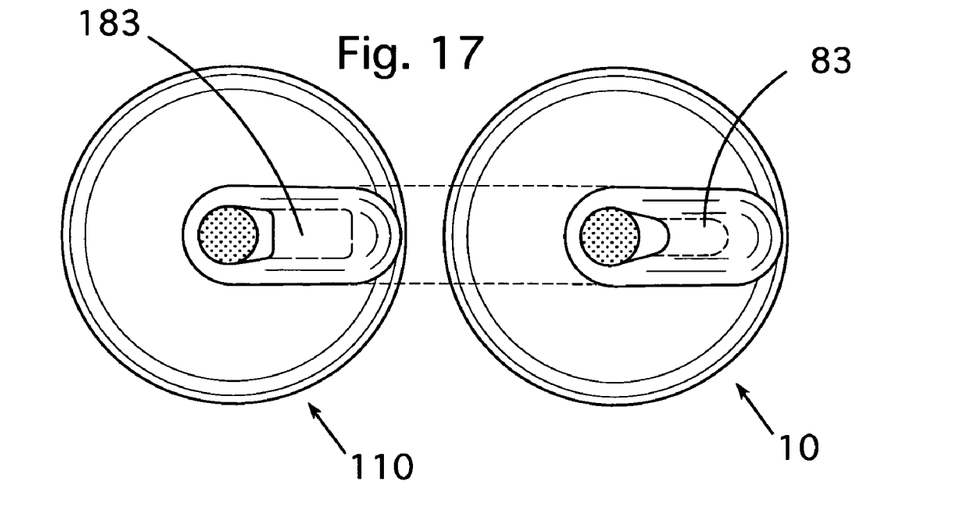
FIG. 17 is a top plan view of the catheter as seen in FIGS. 4 and 14 showing in outline the shapes of the stylet sockets for the first version shown in FIG. 1, and the second version shown in version two in FIG. 11.

FIG. 17 shows a dotted line top plan view of the internal shape of sockets 83 and 183.

Figure 18:
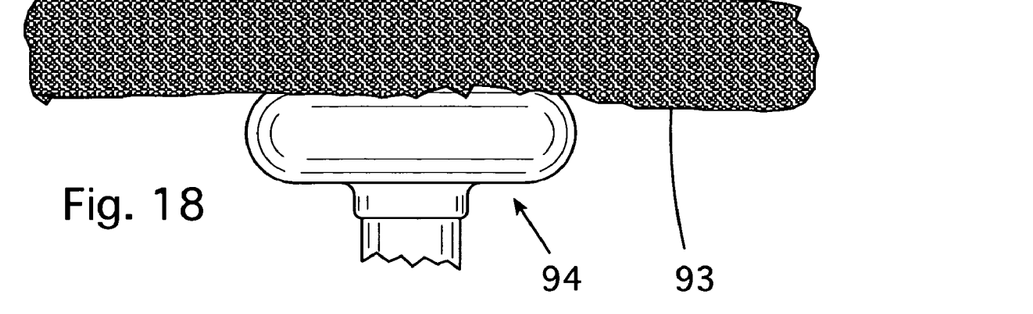
FIG. 18 is a front elevational view of a retention balloon as seen in PEG tubes without a tip bolus showing gastric mucosa occluding the port.
Figure 19:
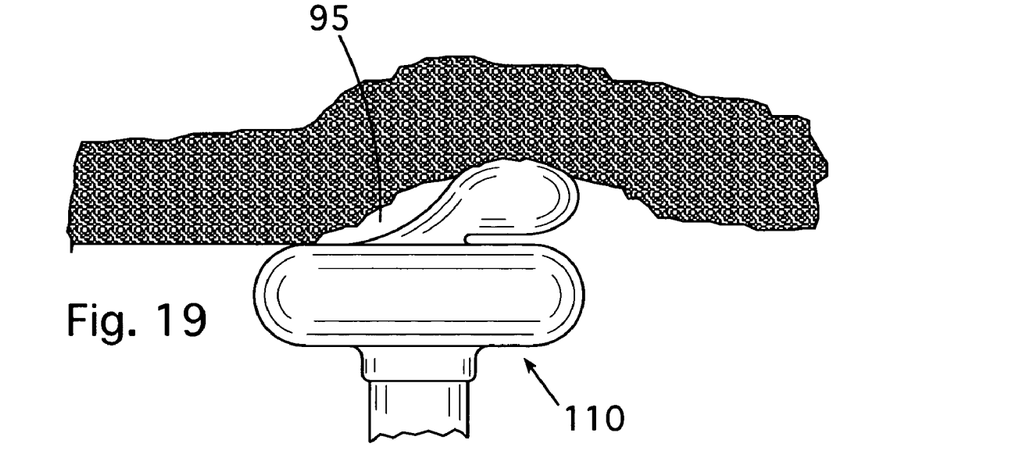
FIG. 19 is a side elevational view of the catheter, similar to FIG. 11, showing the gastric mucosa being held away from the port opening.
Figure 20:
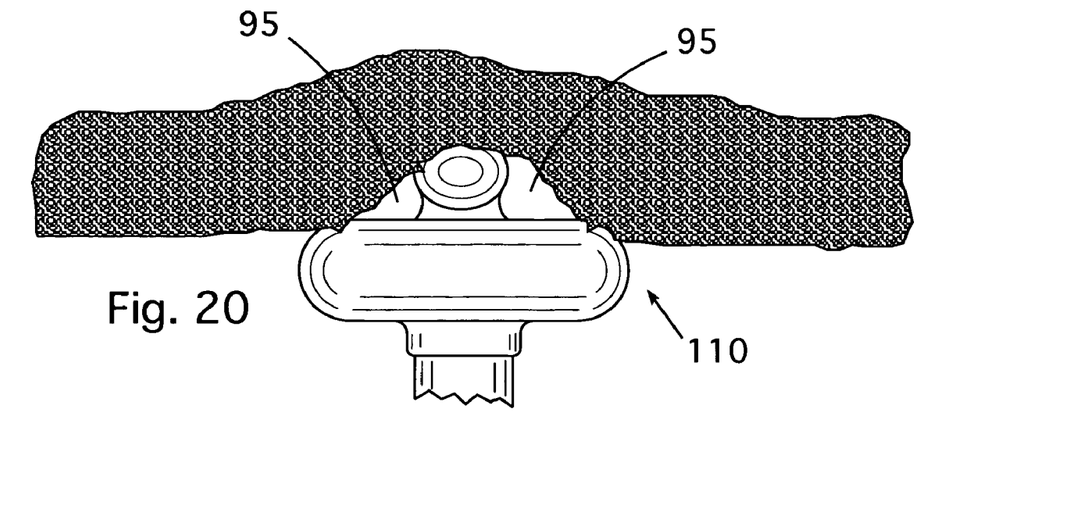
FIG. 20 is a rear elevational view of the catheter end as shown in FIG. 12 showing the gastric mucosa being held away from the port.

FIG. 18 shows mucosa 94 occluding a standard PEG type port. FIGS. 19-20 shows the open spaces 95 created by the tip 116 of assembly 110.

Figure 21:
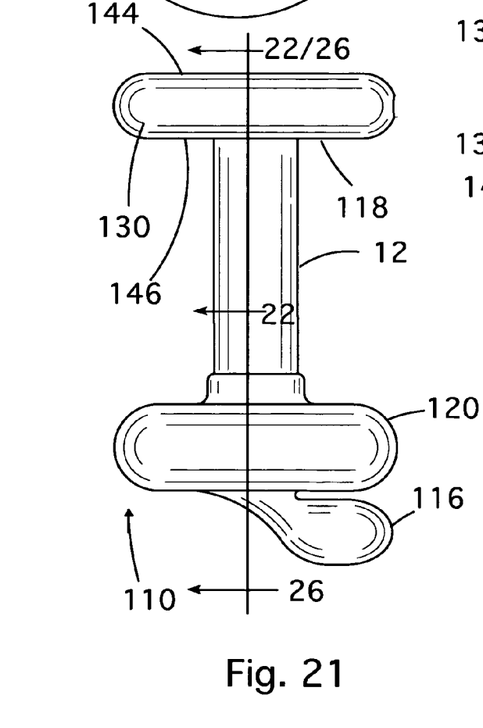
FIG. 21 is a side elevational view of catheter as shown in FIG. 11, but completed with the addition of the external proximal bolster.
Figure 22:
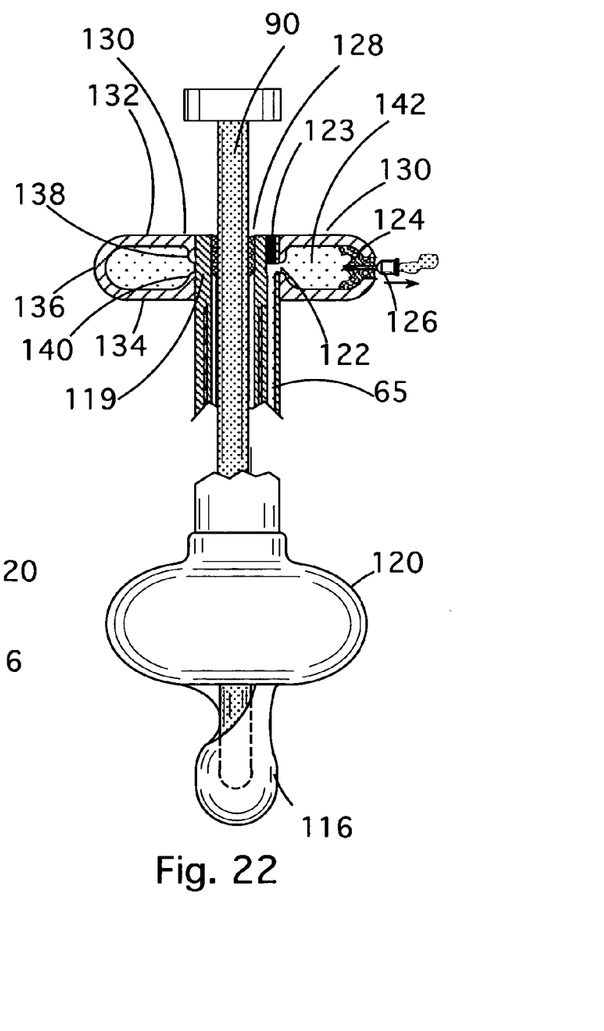
FIG. 22 is a partial sectional view of the catheter as seen in FIG. 21 taken along lines 22-22 of FIG. 21 and a partial side elevational view of FIG. 21 showing the bolus tip 116 and internal bolster 120 being stretched for insertion and air being expelled out of the catheter internal retention bolus 120.
Figure 23:
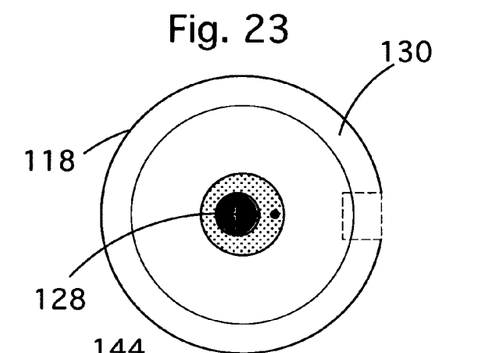
FIG. 23 is a top plan view of the catheter as shown in FIG. 21 showing the valved port for the administration set.

FIGS. 21, 22 and 23 show the external bolster 118. The external bolster has the same basic construction as the internal bolster 116. It attaches to tube 12 at section 119 which has no spring reinforcement. The deflation lumen 65 communicates with the inside of bolster 118 through radial aperture 122 in the tube segment body 41. A plug 123 is placed in the proximal end of the deflation lumen 65 to prevent the escape of air. The external bolster 118 contains silicone slit valve 124 that accepts a blunt tip needle 126 to allow air to enter the system connecting the proximal external bolster 118 with the distal internal bolster 116. Bolster 118 also contains, at the axial midpoint, another silicone slit valve 128 that accepts an access enteral feeding set (not shown) or a urologic drainage set.

Now referring to FIGS. 21, 22 and 23 the external proximal bolster 118 contains a tire shaped balloon 130. As is the internal bolster balloon 120, the balloon 130 is preformed in that shape from silicone rubber and includes parallel walls 132 and 134. The side wall 132 is the top most proximal wall and the side wall 134 is the bottom wall. Connecting the side walls 132 and 134 (in the language of tire construction) is the treadwall 136. The treadwall 136 is semi-circular in construction.

The annular inner peripheries of the side walls 132 and 134 are defined by beads 138 and 140, respectively. Each of the beads 138 and 140 comprises a cylindrical sleeve. The sleeve 138 extends below the top side wall 132. Thus it is inside the balloon 130. The sleeve 140 extends above the bottom wall 134. Thus it is also inside the balloon. The cylindrical inner surfaces of the sleeves 138 and 140 are glued to the outer surface of the tube body 22 wall with a silicone adhesive.

Air is trapped in the space 142 within the preformed balloon 130 when the bead sleeves 138 and 140 are glued to the body 22 to assemble the tube 12 and balloon 130. The top and bottom walls 132 and 134 extend parallel to each other from their corresponding bead sleeves 138 and 140 to their juncture with the semi circular treadwall 138. A top flat surface is 144 is, accordingly, defined on the top outer wall 132 while a flat surface 146 is defined on the bottom wall 134 which is in contact with the patient's skin.

According to the invention, the flat bottom surface 146 forms the external retention surface for catheter 110 and is contact with the patient's skin. The flat top surface 140 is flush with the top of tube 12 at the point that it contains slit valve 128. Thus, the tube 12 does not protrude above the surface of balloon 130.

Figure 24:
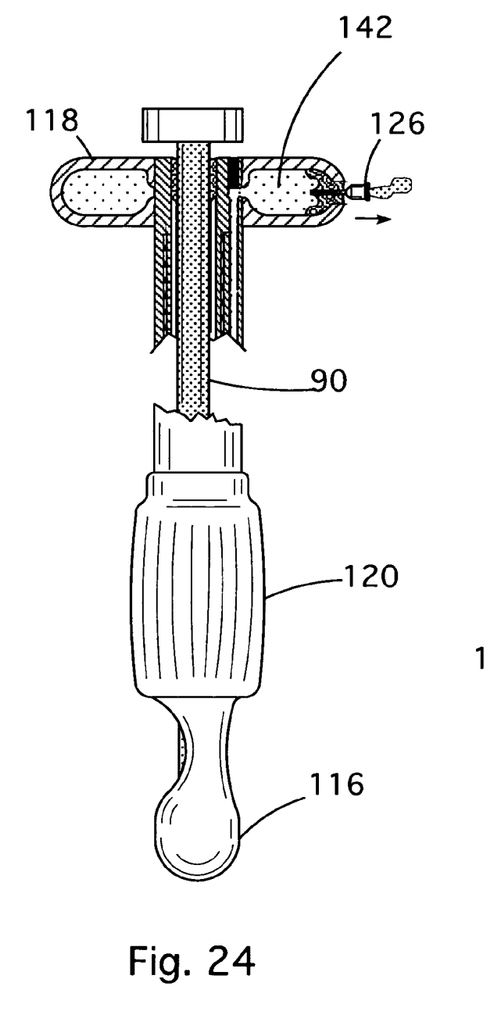
FIG. 24 is a partial sectional view of the catheter as seen in FIG. 21 taken along lines 22-22 of FIG. 21 and a partial side elevational view of FIG. 21 showing the bolus tip in its final stretched position for insertion.
Figure 25:
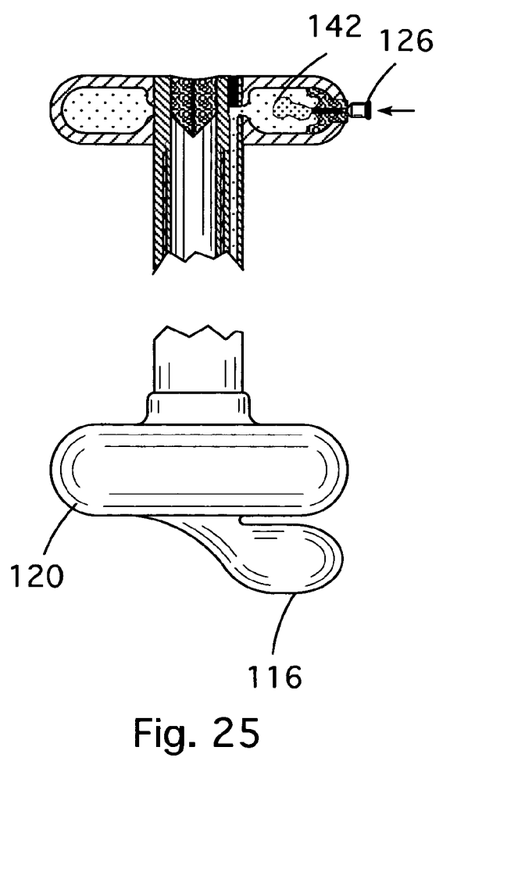
FIG. 25 is a partial sectional view of the catheter as seen in FIG. 21 taken along lines of 22-22 of FIG. 21 and a partial side elevational view of FIG. 21 shown with the stylet removed and the bolus in its final relaxed position showing air re-entering the catheter.
Figure 26:
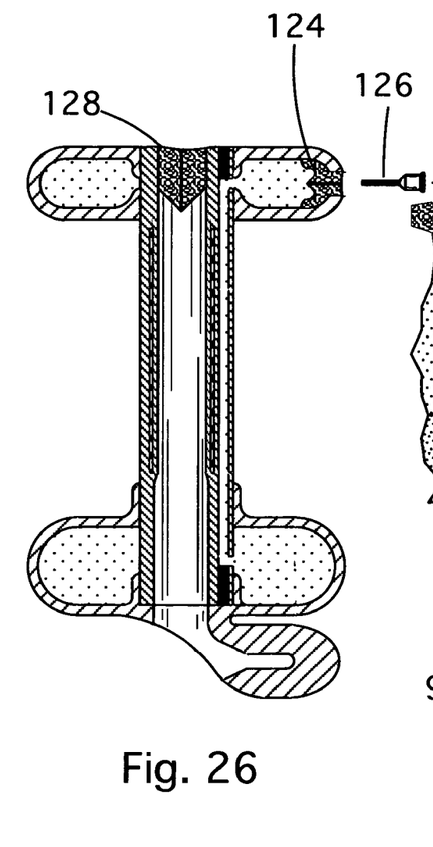
FIG. 26 is a sectional view of the catheter seen in FIG. 21, taken along the line 22-22; showing the blunt needle removed trapping the air in the inflated catheter of FIG. 21, and showing the blunt needle being removed.
Figure 27:
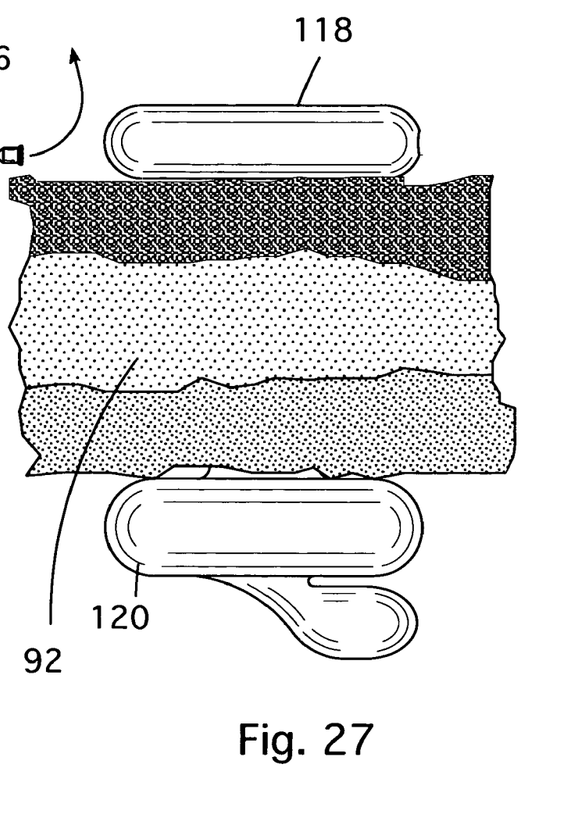
FIG. 27 is a side elevational view of the catheter 21, in-situ.

Now also referring to drawings 21, 22 and 23, a blunt needle 126 is inserted into external balloon 130 through slit valve 124 to allow the escape of air from the internal bolus balloon 120 as the balloon is gradually deformed by the stylet. FIG. 24 shows the balloon 120 fully deflated and deformed and ready for insertion. FIG. 25 shows the balloon in its final in-situ shape after placement and the re-entry of air as the balloon 120 returns to its preformed shape when the stylet is removed after placement. FIG. 26 shows the device 110 in place and the blunt needle 124 removed thereby trapping air in the balloon 120 and 118. FIG. 27 shows the device 110 in place in the patient's body 92 with the external balloon 118 against the patient's skin and the internal retention balloon 2120 against the stomach mucosa.

With the invention placed in-situ feeding or drainage can be started by placing an appropriate feeding set into the slit valve 128 that is glued into top balloon bolster 118.

To remove the catheter after it is no longer required, simply place a small cut in the external balloon 118, thereby allowing the air in the internal balloon bolus 116 to escape and thereby deform the balloon as the catheter is gently pulled out.

The invention claimed is:

1. A catheter comprising:
   a) a catheter tube having a proximal end and a distal end, said tube having a fluid passage lumen therein extending to a port in said distal end;
   b) a retention bolster comprising an annular balloon mounted on said tube adjacent said distal end and normally extending radially outwardly from said tube, said radially extending balloon normally being inflated by air trapped therein; and
   c) a bolus mounted on said distal end of said tube, said bolus being fastened to said tube adjacent said port and cantilevered to one side of said tube and the axis of the distal end port, said bolus normally extending substantially parallel to said retention bolster and, when relaxed, being spaced from said retention bolster and movable independently of said bolster, said bolus also including a tip extending radially to one side of said tube and a resiliently flexible arm connecting said tip to said tube;
   d) said bolus tip having an external nose and containing a socket opposite said nose for receiving a stylet.

2. The catheter of claim 1 further characterized in that:
   a) said arm is flexible in a manner which permits said socket in said tip to be moved independently away from said bolster and from said normally radially extending tip alignment into axial alignment with said lumen adjacent said distal end.

3. The catheter of claim 2 further characterized in that:
   a) said resiliently flexible arm includes opposed side walls bracketing said port.

4. The catheter of claim 2 further characterized in that:
   a) said socket is relatively wide and relatively low in cross-section whereby it is oblong in cross-section.

5. The catheter of claim 2 further characterized in that:
   a) said tube comprises a soft resilient plastic containing a wire coil spring extending to a location in said tube immediately adjacent the bolster balloon; and
   b) said bolster balloon surrounding a tube portion which does not contain a wire coil spring.

6. The catheter of claim 1 further characterized in that:
   a) said tip is normally cantilevered radially to one side of said tube whereby said socket is oriented generally perpendicular to said tube when said resiliently flexible arm is relaxed so that said tip is retracted to said one side of said axis; and
   b) with said tip in said normally cantilevered position, said port is shielded from occlusion of said port by gastric mucosa or the like.

7. The catheter of claim 6 further characterized in that:
a) said flexible arm resiliently flexes under stress to bring said socket into alignment with said axis of said tube at said distal end when a stylet is inserted into said socket.

8. The catheter of claim 1 further characterized in that:
a) said balloon is connected to a passage in said tube for deflating said balloon.

9. The catheter of claim 8 further characterized in that:
a) said passage contains a valve therein.

10. The catheter of claim 9 further characterized in that:
a) said valve is a slit valve.

11. A catheter comprising:
a) a catheter tube having a proximal end and a distal end, said tube having a fluid passage lumen therein extending to a port in said distal end;
b) a retention bolster comprising an annular balloon mounted on said tube adjacent said distal end and normally extending radially outwardly from said tube, said radially extending balloon being inflated by air trapped therein;
c) a bolus mounted on said distal end of said tube, said bolus being fastened to said tube adjacent said port and cantilevered to one side of said tube and the axis of the distal end port, said bolus being spaced from said retention bolster and movable independently from said bolster;
d) said bolus including a tip normally extending radially to one side of said tube and a resiliently flexible arm connecting said tip to said tube, said bolus tip having an external nose and containing a socket opposite said nose for receiving a stylet;
e) said arm flexing in a manner which permits said socket in said tip to be moved independently of said bolster from said normally radially extending tip alignment into axial alignment with said lumen adjacent said distal end;
f) said resiliently flexible arm including opposed side walls bracketing said port, said flexible arm resiliently flexing under stress to bring said socket into alignment with said axis of said tube at said distal end when a stylet is inserted into said socket;
g) said tip being normally cantilevered radially to one side of said tube whereby said socket is oriented generally perpendicular to said tube when said resiliently flexible arm is relaxed so that said tip is retracted to said one side of said axis and said tip in said normally cantilevered position shields said port from occlusion of said port by gastric mucosa or the like.

12. A method of inserting the catheter of claim 1, 2, or 11 through a body cavity opening into the cavity, comprising the steps of:
a) bending said resiliently flexible arm until said socket is in axial alignment with said lumen adjacent said port;
b) inserting a stylet through said lumen from the proximal end of said tube until said stylet protrudes from said port and seats in said socket, whereby said tube inside said bolster balloon is stretched axially and said balloon is reduced in diameter radially while said tip is held in a position extended axially of said tube by said stylet;
c) inserting said tip in said opening and forcing said bolus and said axially stretched balloon bolster through said opening into said cavity; and
d) retracting said stylet whereby said tip resiliently returns automatically to its original, radially extending relaxed position.

* * * * *